United States Patent
Patel et al.

(10) Patent No.: US 6,947,581 B1
(45) Date of Patent: Sep. 20, 2005

(54) INTEGRATED DATA CONVERSION AND VIEWING STATION FOR MEDICAL IMAGES

(75) Inventors: Maqbol Patel, Bangalore (IN); David McKone, Ann Arbor, MI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/473,003

(22) Filed: Dec. 28, 1999

(51) Int. Cl.[7] .............................................. G06K 9/00
(52) U.S. Cl. ...................... 382/128; 382/303; 382/305; 707/10
(58) Field of Search ............................... 382/128–132, 382/303, 305; 707/1, 6, 10, 104

(56) References Cited

U.S. PATENT DOCUMENTS

| | | | |
|---|---|---|---|
| 4,652,999 A | | 3/1987 | Higashi et al. |
| 5,542,003 A | * | 7/1996 | Wofford ...................... 382/132 |
| 5,644,662 A | * | 7/1997 | Vuylsteke ................... 382/302 |
| 5,715,823 A | * | 2/1998 | Wood et al. ................. 358/1.2 |
| 6,231,246 B1 | * | 5/2001 | Takeo et al. ................ 600/437 |

OTHER PUBLICATIONS

Fuji CR Processing web pages (22 pages), author unknown, date unknown, <http://www.fujindt.com/medical>, printed Nov. 18, 1999.

"PACS Basic Principles and Applications", H. K. Huang, D.Sc., Chapters 7, 8, 12, pp. 199-231, 305-342, 177-198.

* cited by examiner

Primary Examiner—Jon Chang
Assistant Examiner—Charles Kim
(74) Attorney, Agent, or Firm—McAndrews, Held & Malloy, Ltd.; Peter J. Vogel; Michael A. Dellapenna

(57) ABSTRACT

A method, in a picture archiving and communication system (PACS), for processing raw image data at a PACS display workstation includes the step of retrieving from a PACS database raw image data delivered from an imaging modality. The method also includes selecting from a PACS database a first preprocessing function for the raw image data delivered from the imaging modality. The method then processes the raw image data at the PACS display workstation by applying the first preprocessing function to the raw image data to create resultant image data, which may then be stored in the PACS database for future retrieval. A PACS display workstation includes a processing circuit, a PACS network interface coupled to the processing circuit, and a software memory coupled to the processing circuit. The software memory stores instructions for retrieving from a PACS database raw image data delivered from an imaging modality, selecting from a PACS database a first preprocessing function for the raw image data delivered from the imaging modality, and processing said raw image data at the PACS display workstation by applying the first preprocessing function to the raw image data.

25 Claims, 6 Drawing Sheets

INTEGRATED DATA CONVERSION AND VIEWING STATION FOR MEDICAL IMAGES

BACKGROUND OF THE INVENTION

This invention relates to picture archiving and communications systems, and more particularly relates to image viewing and manipulation workstations for use in such systems.

Picture archiving and communication systems (PACS) connect to medical diagnostic imaging devices and employ an acquisition gateway (between the acquisition device and the PACS), storage and archiving units, display workstations, databases, and sophisticated data processors. These components are integrated together by a communication network and data management system. A PACS has, in general, the overall goals of streamlining health-care operations, facilitating distributed remote examination and diagnosis, and improving patient care.

PACS have only recently been introduced to the medical community. A reflection of their recent appearance may be seen in limitations inherent with many of the components used to build a PACS. As an example, the acquisition gateway that acquires raw image data from an imaging modality initially modifies the raw image data using preprocessing functions (as one example, FUJI preprocessing functions). The preprocessing functions modify the raw image data for contrast and frequency enhancements, for example, and the acquisition gateway further converts the resultant image data into a PACS compliant format, for example DICOM format. The preprocessing functions initially applied by the acquisition gateway bar the reapplication of the preprocessing functions at the display workstation. Thus, the display workstations coupled to the PACS are unable to perform sophisticated image modifications possible only by applying the preprocessing functions to the raw image data.

In other words, the display workstations used in PACS are adapted only for viewing fully preprocessed image data and performing limited image modification (e.g., contrast enhancement, edge detection, and cropping only on the image data in PACS compliant format). An initial image preprocessing decision is thereby imposed upon all subsequent viewers of the image, including, for example, doctors who will use the image to diagnose a patient. While a preprocessed image may, in fact, be adequate for a particular examination, such preprocessing eliminates the possibility for custom manipulation of the raw image data as an additional aid in diagnosis.

This invention addresses this problem and provides a solution.

BRIEF SUMMARY OF THE INVENTION

A preferred embodiment of the present invention includes a method, in a picture archiving and communication system (PACS), for processing raw image data at a PACS display workstation. The method includes the step of retrieving from a PACS database, using a PACS workstation, raw image data delivered from an imaging modality. The method also includes selecting from a PACS database, using the PACS workstation, a first preprocessing function for the raw image data delivered from the imaging modality. The preprocessing function is characterized in that [ ]. The method then processes the raw image data at the PACS display workstation by applying the first preprocessing function to the raw image data to create resultant image data, which may then be stored in the PACS database for future retrieval.

A preferred embodiment of the present invention also includes, in a picture archiving and communication system (PACS), a PACS display workstation. The workstation includes a processing circuit, a PACS network interface coupled to the processing circuit, and a software memory coupled to the processing circuit. The software memory stores instructions for execution by the processing circuit for retrieving from a PACS database raw image data delivered from an imaging modality, selecting from a PACS database a first preprocessing function for the raw image data delivered from the imaging modality, and processing said raw image data at the PACS display workstation by applying the first preprocessing function to the raw image data.

DETAILED DESCRIPTION OF THE INVENTION

Figure 1:
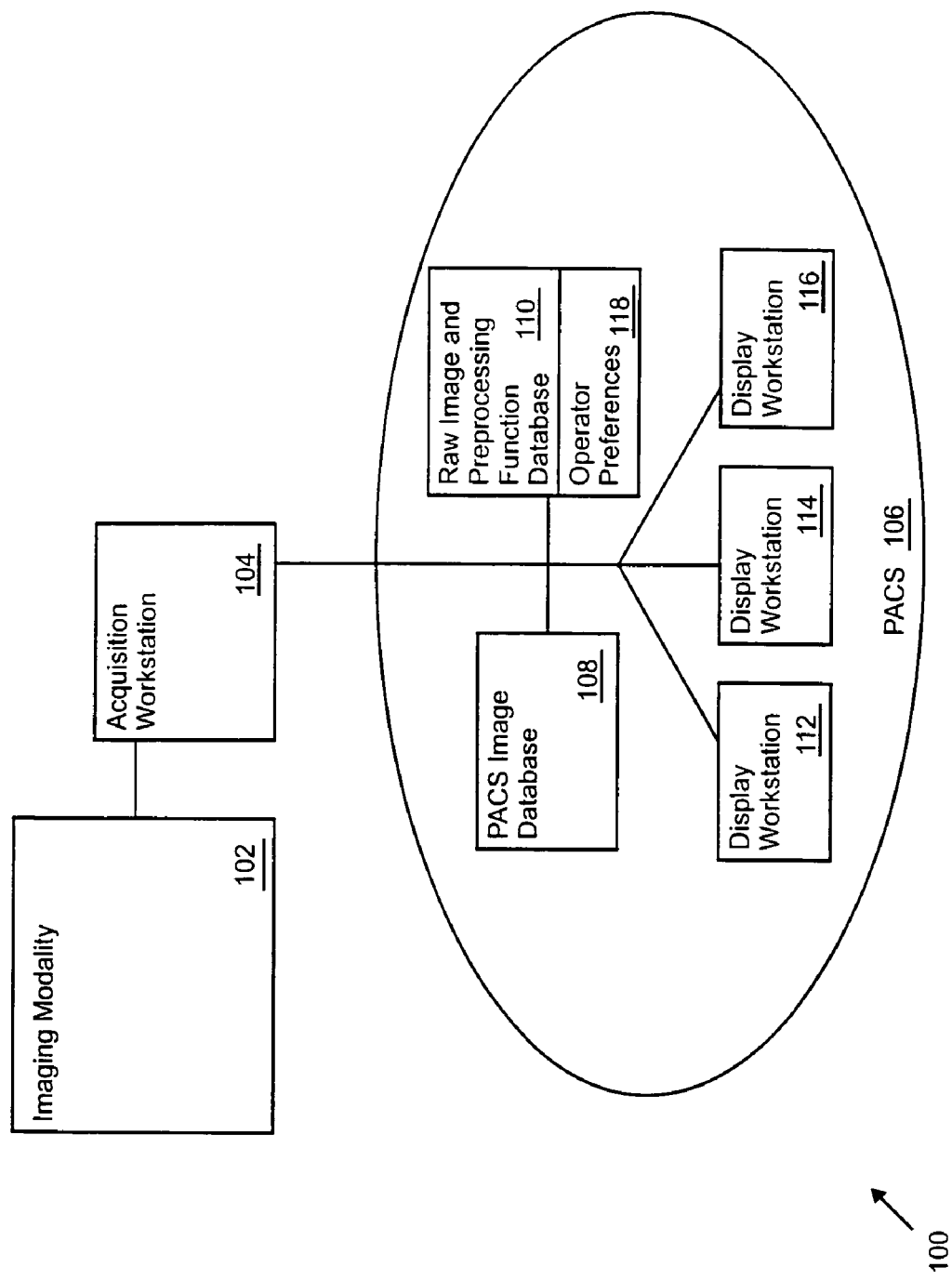
FIG. 1 presents a high level block diagram of a PACS system.

Turning now to FIG. 1, that figure shows a medical data network 100 including an imaging modality 102, an acquisition workstation 104, and a PACS network 106. The PACS network 106 includes a PACS image database 108, a raw image data and preprocessing function database 110 ("preprocessing database 110"), and display workstations 112, 114, 116. A set of operator preferences 118 is stored in the preprocessing database 110.

The imaging modality 102 is generally a medical diagnostic imaging device. For example, the imaging modality 102 may be an X-ray imager, ultrasound scanner, magnetic resonance imager, or the like. The imaging modality 102 generates raw image data as a result of an examination. The imaging modality 102 is connected to the acquisition workstation 104 using, for example, a network connection or dedicated interface port.

The acquisition workstation 104 acts as a gateway between the imaging modality 102 and the PACS network 106. To that end, the acquisition workstation 104 accepts raw image data from the imaging modality 102. In turn, the acquisition workstation 104 optionally performs preprocessing on the raw image data (as described in more detail below) in preparation for delivering image data to the PACS network 106 for storage in the PACS image database 108 or preprocessing database 110. In operation, the acquisition workstation 104 may convert the raw image data into a DICOM standard format, attach a DICOM header, and the like.

The PACS image database 108 and the preprocessing database 110 are illustrated in FIG. 1 for convenience as separate databases. However, they may be a single database, separate databases on an single computer, or separate databases distributed among different computers. In general, the PACS image database 108 stores fully preprocessed images (i.e., those images for which no additional preprocessing functions will be applied). On the other hand, the preprocessing database 110 stores partially preprocessed image data ("raw image data") (i.e., that image data that has not yet been completely preprocessed).

The display workstations 112–116 are coupled to the PACS image database 108 and the preprocessing database 110. Thus, the display workstations 112–116 may retrieve images from the PACS image database 108 for immediate modification and display, or the display workstations 112–116 may retrieve raw image data from the preprocessing database 110. When the display workstations 112–116 retrieve raw image data, however, the raw image data is further modified by preprocessing functions to form resultant image data. The resultant image data may then represent a fully preprocessed image, or may require additional preprocessing before being stored as a fully preprocessed image.

The preprocessing functions are characterized in that they are modality specific enhancements (e.g., contrast or frequency compensation functions specific to a particular X-ray imaging device, for example) applied at the beginning of the imaging and display chain. The preprocessing functions differ from the processing functions applied to fully preprocessed images in that the processing functions are not modality specific and are instead applied the end of the imaging and display chain.

Figure 2:
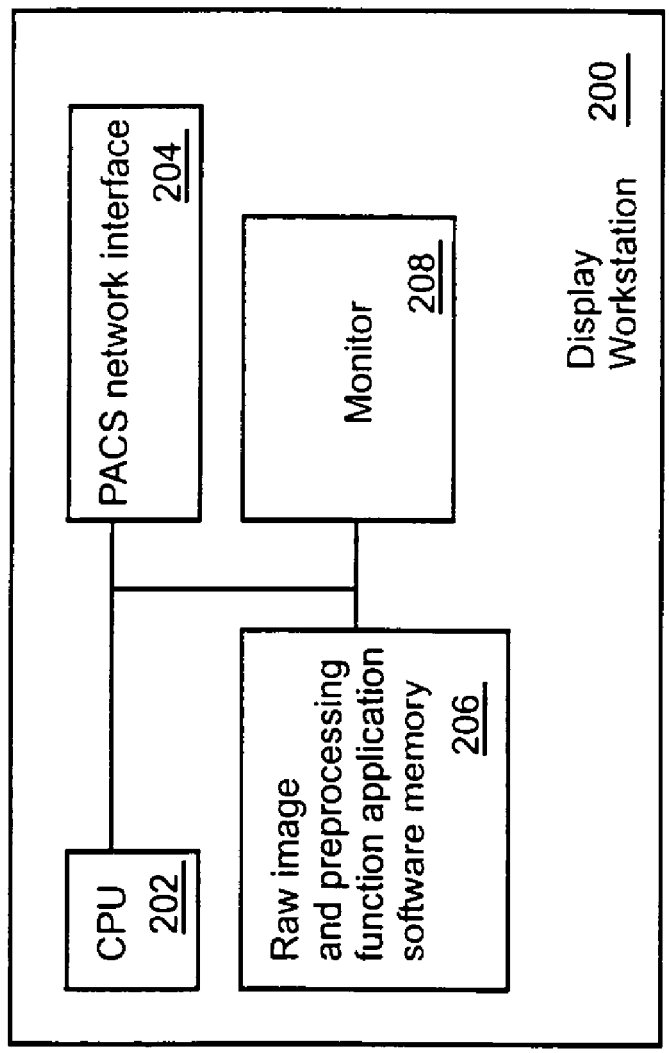
FIG. 2 illustrates a PACS display workstation for processing raw image data.

Turning now to FIG. 2, that figure illustrates a PACS display workstation 200 suitable for use in the PACS network 106. The display workstation 200 includes a general purpose processing circuit 202, a PACS network interface 204, a software memory 206, and an image display monitor 208. The PACS network interface 204 is generally implemented as a network card connecting to a TCP/IP based network, but may also be implemented as a parallel port interface, or the like. In particular, the software memory 206 is a raw image and preprocessing function software memory.

Thus, the software memory 206 includes, for execution by the processing circuit 202, instructions for retrieving, from a PACS database, raw image data delivered from an imaging modality. The instructions also allow the operator at the PACS workstation 200 to select a preprocessing function for the raw image data. Once the raw image data and the preprocessing function are determined, the instructions in the software memory 206 allow the processing circuit 202 to apply the preprocessing function to the raw image data to create resultant image data.

As an example, the raw image data may be frequency preprocessed raw image data or contrast preprocessed raw image data. In other words, the acquisition workstation 104 may have already performed a limited preprocessing of the raw image data and stored the results in the preprocessing database 110. In a preferred embodiment, the acquisition workstation 104 applies a subset of predetermined preprocessing functions (e.g., frequency preprocessing functions) to the raw image data, allowing the remaining preprocessing functions (e.g., contrast preprocessing functions) to be applied by the PACS workstations 112–116 that thereby generate a fully preprocessed image. Raw image data therefore may be regarded as image data initially acquired from an imaging modality and that has not been fully preprocessed according to predetermined set of preprocessing functions (e.g., the FUJI preprocessing functions).

In selecting the preprocessing function, the PACS workstation 200 allow the operator to choose one or more remaining preprocessing functions (e.g., frequency or contrast preprocessing functions) for application to the raw image data to generate resultant image data. The resultant image data may be stored in the preprocessing database 110 for future preprocessing, or, if all preprocessing has been accomplished, the resultant image data may be stored in the PACS image database 108 for future processing and display.

In other words, once the resultant image data has been fully preprocessed, conventional image processing algorithms may be applied. The processed resultant image data may then be displayed on the image display monitor 208.

One specific example of preprocessing functions are the industry standard FUJI Computed Radiography (CR) modality preprocessing functions. The FUJI preprocessing functions include contrast preprocessing functions and frequency preprocessing functions. The contrast preprocessing functions are characterized by the following parameters: GT (contrast type), GA (rotation amount of GT curve), GC (rotation center for GT), and GS (density shift, the amount of shifting applied to GT). The frequency preprocessing functions are characterized by the following parameters: RN (frequency rank), RE (frequency enhancement), and RT (frequency type). Each preprocessing function may represent a linear or non-linear function, function modification, or function parameter. The preprocessing functions may be applied to raw image data any time prior to the image processing and display.

The preprocessing functions may be selected based, for example, on an anatomical region to which the raw image data corresponds. In other words, the preprocessing functions selected may vary depending on whether the raw image data represents, as examples, the head, neck, chest, abdomen, breast, lungs, pelvis, or shoulders. The preprocessing functions may vary for each anatomical region due to the differences in tissue, bone, and blood vessel density and prevalence.

The display workstations 112–116 preferably allow their operator to save operator preferences in the PACS system 106 for future retrieval and subsequent application. As an example, the display workstations 112–116 may identify an operator by login name or by querying the operator for an identification code. As the operator works with the preprocessing functions, the operator may develop a preference for application of specific preprocessing functions. The display workstations 112–116 save the operator preferences 118 in, for example, in the preprocessing database 110. When the operator logs in at a later time, the display workstations 112–116 query the database for the operator preferences 118 (e.g., based on login name or operator ID) and retrieve any preferences found.

The display workstations 112–116 may then apply the retrieved operator preferences 118 by default to any raw image data currently retrieved by the display workstations 112–116. The operator preferences 118 may include additional information other than the preferred preprocessing functions, including screen resolution, image layout and position, and color information. Furthermore, the operator preferences 118 may additional be stored based on anatomical areas of interest. For example, the operator preferences 118 may include the default preprocessing functions to be applied for neck images, and the default preprocessing functions to be applied for chest images.

Figure 3:
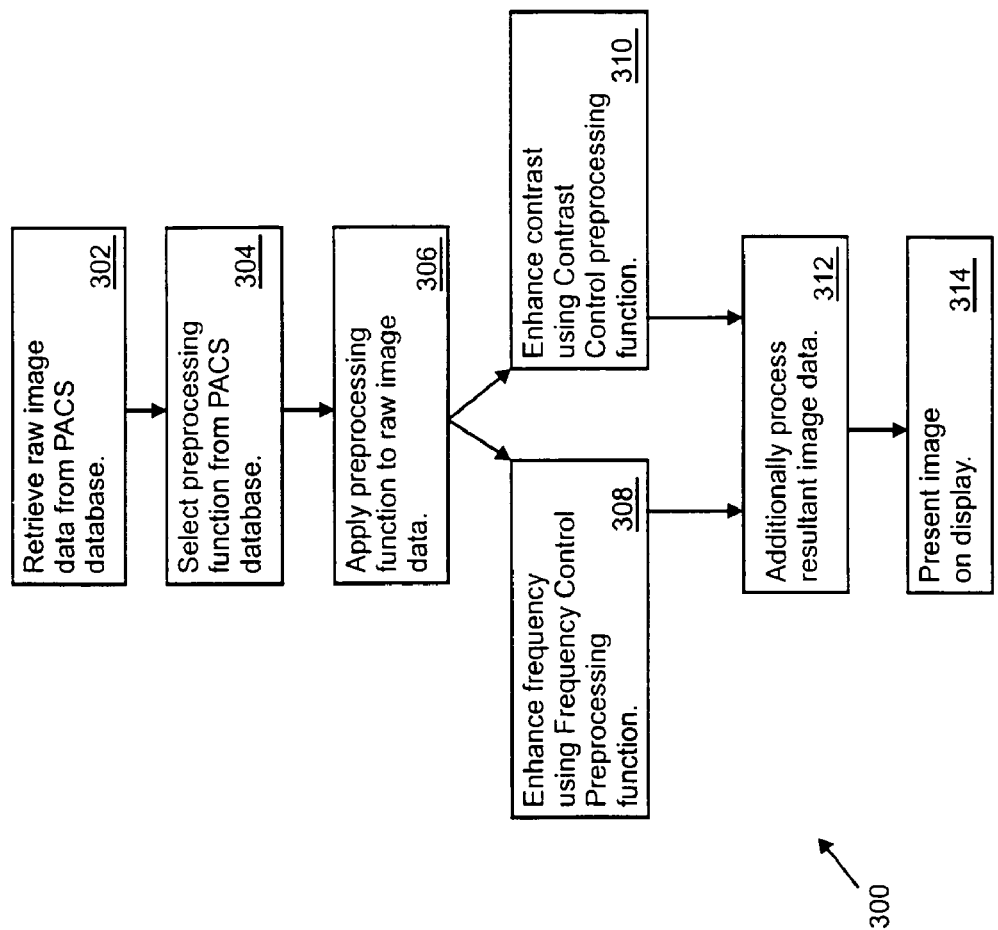
FIG. 3 illustrates a flow diagram of a method for processing raw image data delivered from an imaging modality.

Turning now to FIG. 3, that figure illustrates a flow diagram 300 of a method for processing raw image data, and the software steps executed by the processing circuit 202. At step 302, the processing circuit 202 (e.g., manually under operator control or automatically in accordance with an automated processing script) retrieves raw image data from the preprocessing database 110. Subsequently, the processing circuit 202 selects (manually or automatically) a preprocessing function from the preprocessing database 110 (step 304). During step 306, the processing circuit 202 applies the preprocessing function to the raw image data. As examples, the preprocessing function may include frequency control preprocessing (step 308) or contrast control preprocessing (step 310).

After the preprocessing functions are finished, the processing circuit 202 may then apply additional image processing techniques (e.g., edge detection, edge enhancement, noise reduction, image cropping, contrast enhancement, and the like) to the fully processed resultant image data (step 312). At step 314, the processed resultant image data is displayed.

Figure 4:
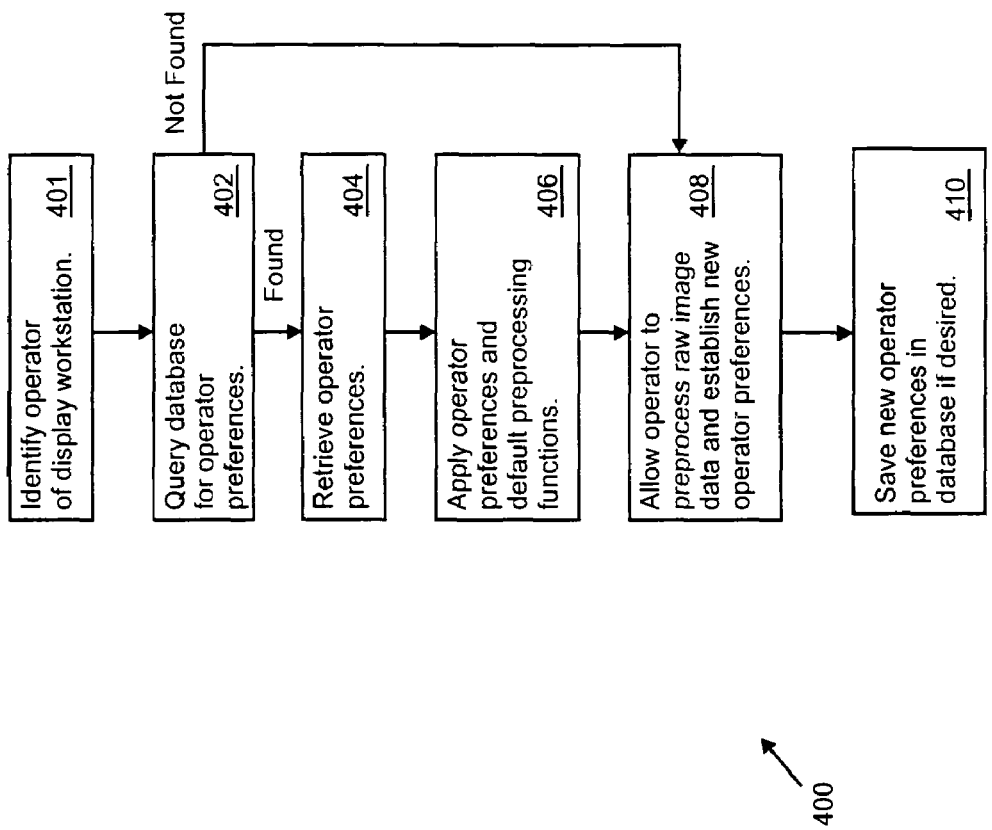
FIG. 4 shows a flow diagram of a method for default processing of operator preferences.

Before an operator at a display workstation 112–116 begins work, the display workstations 112–116 may retrieve and apply default operator preferences. Turning now to FIG. 4, that figure shows a flow diagram 400 of the steps that a display workstation 112–116 executes to apply the default operator preferences. At step 401, the display workstation 112–116 identifies the operator using, for example, a login name and password. Next, at step 402, the display workstation 112–116 queries a database for operator preferences 118. If operator preferences 118 do not exist, then processing continues at step 408. If operator preferences 118 do exist, then the display workstation 112–116 retrieves the operator preferences 118 (step 404). Subsequently, at step 406, the display workstation 112–116 applies the operator preferences 118 (e.g., screen resolution, image layout, colors, and the like), and in particular applies the preprocessing function preferences as defaults to the current raw image data that the operator is working with.

Continuing at step 408, the display workstation 112–116 allows the operator to continue to preprocess the raw image data and to process fully preprocessed image data. The operator may also adjust the operator preferences, such as screen size, image orientation, preprocessing function preference, and the like. In other words, the display workstation 112–116 allows the operator to establish new operator preferences (step 408). When the operator is finished using the display workstation 112–116, the display workstation 112–116 saves the (possibly new or revised) operator preferences in a database, if the operator so instructs the display workstation 112–116 (step 410).

Figure 5:
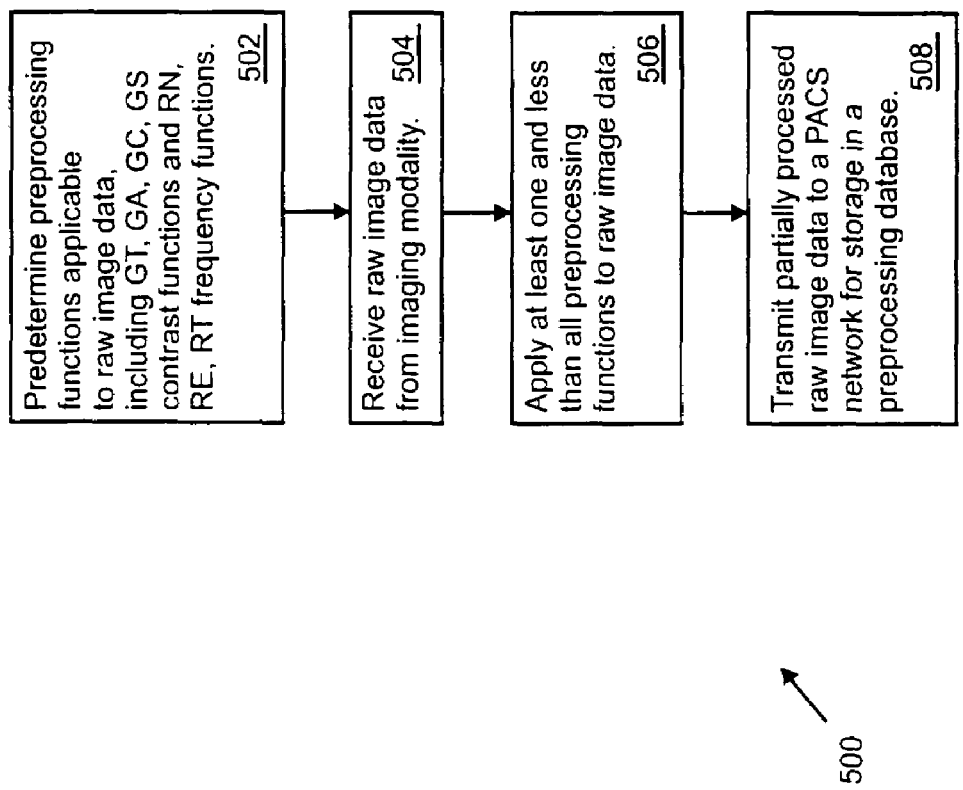
FIG. 5 depicts a flow diagram of a technique for partially preprocessing raw image data delivered from an imaging modality.

As noted above, the acquisition workstation 104 may apply a subset of predetermined preprocessing functions (e.g., frequency preprocessing functions) to the raw image data, allowing the remaining preprocessing functions (e.g., contrast preprocessing functions) to be applied by the PACS workstations 112–116 that thereby generate a fully preprocessed image. Turning now to FIG. 5, that figure illustrates a flow diagram 500 of the processing that occurs at an acquisition workstation 104. An initial step (step 502) is taken to store predetermined preprocessing functions at the acquisition workstation 104 (e.g., by storing functions, lookup tables, piecewise linear curve approximations, curve parameter values, and the like).

Next, at step 504, the acquisition workstation 104 receives raw image data from an imaging modality. Subsequently, the acquisition workstation 104 preferably applies at least one, but less than all preprocessing functions to the raw image data (step 506) to form partially preprocessed raw image data. The display workstations 112–116 may thereby complete the image preprocessing on the partially preprocessed raw image data using the flexible preprocessing functions. When the acquisition workstation 104 is finished, it transmits the partially preprocessed raw image data to the PACS network 106 for storage in the preprocessing database 110 (step 508).

Figure 6:
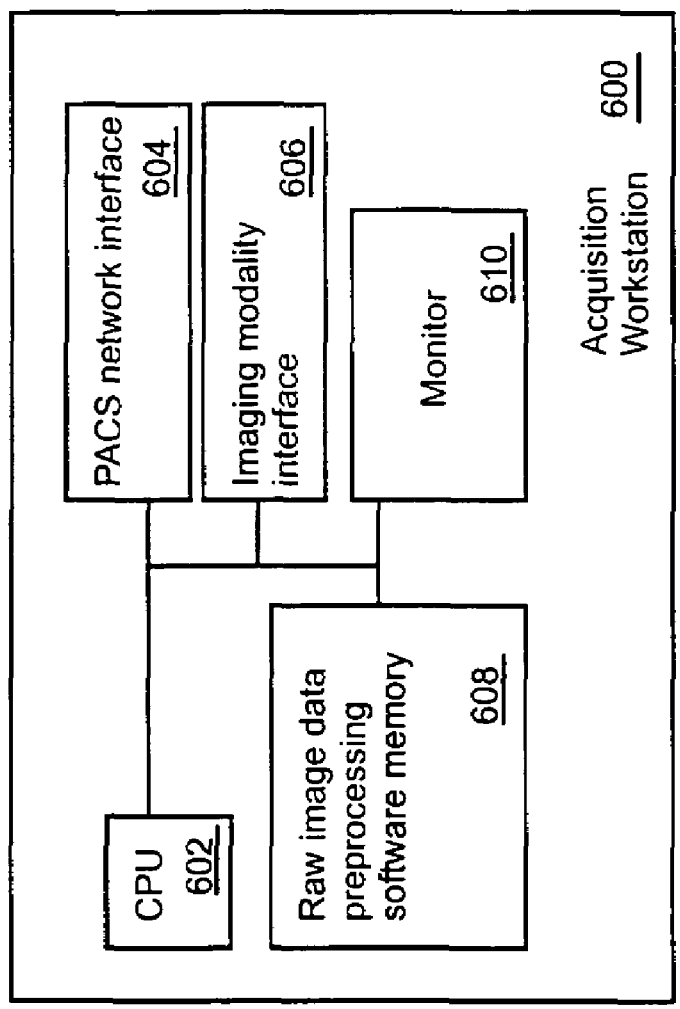
FIG. 6 shows a block diagram of an acquisition workstation.

Turning now to FIG. 6, that figure illustrates one embodiment of an acquisition workstation 600 suitable for use with the PACS network 106. The acquisition workstation 600 includes a processing circuit 602, a PACS network interface 604, and an imaging modality interface 606. The acquisition workstation 600 also includes a software memory 608, and an image display monitor 610. The PACS network interface 604 and imaging modality interface 606 are generally implemented as network cards connecting to a TCP/IP based network, but may also be implemented as parallel port interfaces, proprietary hardwired or wireless interfaces, or the like.

The software memory 608, in particular, is a raw image data preprocessing software memory. Thus, the software memory 608 includes, for execution by the processing circuit 602, instructions for performing the functions described above in the flowchart of FIG. 5. In other words, the acquisition workstation 600 receives raw image data over the imaging modality interface 606, partially preprocesses the raw image data to form partially preprocessed raw image data, and transmits the partially preprocessed raw image data through the PACS network interface 604 to the PACS network 106.

The raw image data preprocessing method and PACS workstation of the preferred embodiment thus provide much more extensive and detailed image modification possibilities to the display workstation operator. The present method and workstation thus remove the initial image preprocessing decisions imposed by prior systems upon all subsequent viewers of the image. Thus, doctors and technicians may perform custom manipulation of the raw image data as an additional aid in diagnosis.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. In a picture archiving and communication system (PACS), a method of processing image data at a PACS display workstation, the method comprising:

retrieving from a PACS database, using a PACS display workstation, partially preprocessed raw image data, said partially preprocessed raw image data having been partially preprocessed according to a predetermined subset of preprocessing functions obtained from a set of preprocessing functions comprising at least contrast and frequency preprocessing functions, said predetermined subset of preprocessing functions applied to modality raw image data at an acquisition workstation, said modality raw image data delivered from an imaging modality;

selecting from a PACS database, using the PACS display workstation, a first preprocessing function for the partially preprocessed raw image data, wherein said first preprocessing function is stored in said PACS database, said first preprocessing function comprising the remaining subset of preprocessing functions from the set of preprocessing functions not included in said predetermined subset of preprocessing functions; and applying, using the PACS display workstation, the first preprocessing function to the partially preprocessed raw image data to create resultant image data.

2. The method of claim 1, wherein the step of retrieving partially preprocessed raw image data further comprises retrieving frequency preprocessed raw image data.

3. The method of claim 2, wherein the step of selecting further comprises selecting a contrast preprocessing function.

4. The method of claim 3, wherein the step of selecting further comprises selecting a contrast preprocessing function characterized by at least one of a GT, GA, GC, and GS preprocessing parameter.

5. The method of claim 1, wherein the step of retrieving partially preprocessed raw image data further comprises retrieving contrast preprocessed raw image data.

6. The method of claim 5, wherein the step of selecting further comprises selecting a frequency preprocessing function.

7. The method of claim 6, wherein the step of selecting further comprises selecting a frequency preprocessing function characterized by at least one of a RN, RE, and RT preprocessing parameter.

8. The method of claim 1, further comprising the step of applying an image processing function to the resultant image data to create processed resultant image data.

9. The method of claim 8, further comprising the stop of displaying the processed resultant image data.

10. The method of claim 1, further comprising the step of storing the resultant image data in the PACS database for future retrieval.

11. In a picture archiving and communication system (PACS), a PACS display workstation comprising:
a processing circuit;
a PACS network interface coupled to the processing circuit; and
a software memory coupled to the processing circuit, the software memory storing instructions for:
retrieving from a PACS database partially preprocessed raw image data, said partially Preprocessed raw image data having been partially preprocessed according to a predetermined subset of preprocessing functions obtained from a set of preprocessing functions comprising at least contrast and frequency preprocessing functions, said predetermined subset of preprocessing functions applied to modality raw image data at an acquisition workstation, said modality raw image data delivered from an imaging modality;
selecting from a PACS database a first preprocessing function for the partially preprocessed raw image data, wherein said first preprocessing function is stored in said PACS database, said first preprocessing function comprising the remaining subset of preprocessing functions from the set of preprocessing functions not included in said predetermined subset of preprocessing functions; and
applying the first preprocessing function to the partially preprocessed raw image data to create resultant image data.

12. The PACS display workstation of claim 11, wherein the partially preprocessed raw image data corresponds to an anatomical region, and wherein the preprocessing function is selected based on the anatomical region.

13. The PACS display workstation of claim 11, wherein the partially processed raw image data is frequency processed raw image data.

14. The PACS display workstation of claim 13, wherein the preprocessing function is a contrast preprocessing function.

15. The PACS display workstation of claim 14, wherein the contrast preprocessing function characterized by at least one of a GT, GA, GC, and GS preprocessing parameter.

16. The PACS display workstation of claim 11 wherein the partially processed raw image data is contrast preprocessed raw image data.

17. The PACS display workstation of claim 16, wherein the preprocessing function is a frequency preprocessing function.

18. The PACS display workstation of claim 17, wherein the frequency preprocessing function characterized by at least one of a RN, RE, and RT preprocessing parameter.

19. The PACS display workstation of claim 11, wherein the software memory further comprises instructions for applying an image processing function to the resultant image data.

20. The PACS display workstation of claim 1, wherein the software memory further comprises instructions for storing the resultant image data in the PACS database for future retrieval.

21. A medical data network comprising:
an image modality;
an image acquisition workstation;
a PACS network interfaced to the image acquisition workstation, the PACS network comprising a networked PACS image database, a PACS display workstation, and a preprocessing database, and wherein the PACS display workstation comprises:
a processing circuit;
a PACS network interface coupled to the processing circuit; and
a software memory coupled to the processing circuit, the software memory storing instructions for:
retrieving from the preprocessing database partially preprocessed raw image data, said partially preprocessed raw image data having been partially preprocessed according to a predetermined subset of preprocessing functions obtained from a set of preprocessing functions comprising at least contrast and frequency preprocessing functions, said predetermined subset of preprocessing functions applied to modality raw image data at the image acquisition workstation, said modality raw image data delivered from the imaging modality;
selecting from the preprocessing database a first preprocessing function for the partially preprocessed raw image data, wherein said first preprocessing function is stored in said preprocessing database, said first preprocessing function comprising the remaining subset of preprocessing functions from the set of preprocessing functions not included in said predetermined subset of preprocessing functions; and applying the first preprocessing function to the partially preprocessed raw image data to create resultant image data.

22. The medical data network of claim 21, wherein the first preprocessing function is a contrast preprocessing functions.

23. The medical data network of claim 22, wherein the contrast preprocessing function characterized by at least one of a GT, GA, GC, and GS preprocessing parameter.

24. The medical data network of claim 21, wherein the first preprocessing function is a frequency preprocessing function.

25. The medical data network of claim 24, wherein the frequency preprocessing function characterized by at least one of a RN, RE, and RT preprocessing parameter.

* * * * *

UNITED STATES PATENT AND TRADEMARK OFFICE
CERTIFICATE OF CORRECTION

PATENT NO. : 6,947,581 B1
DATED : September 20, 2005
INVENTOR(S) : Patel et al.

It is certified that error appears in the above-identified patent and that said Letters Patent is hereby corrected as shown below:

Column 7,
Line 40, delete "Preprocessed" and insert -- preprocessed --.

Column 8,
Lines 45 to 51 should be indented as lines 34 to 44.
Line 52, after "and" a new paragraph begins with same indentation as lines 34 to 44.

Signed and Sealed this

Twenty-fourth Day of January, 2006

JON W. DUDAS
*Director of the United States Patent and Trademark Office*